(12) United States Patent
Cain et al.

(10) Patent No.: US 7,740,864 B2
(45) Date of Patent: Jun. 22, 2010

(54) VACCINES FOR DISEASES OF FISH

(75) Inventors: Kenneth D. Cain, Moscow, ID (US); Benjamin R. LaFrentz, Auburn, AL (US); Scott LaPatra, Twin Falls, ID (US)

(73) Assignee: University of Idaho, Moscow, ID (US)

( * ) Notice: Subject to any disclaimer, the term of this patent is extended or adjusted under 35 U.S.C. 154(b) by 0 days.

(21) Appl. No.: 12/156,509

(22) Filed: Jun. 2, 2008

(65) Prior Publication Data

US 2008/0317781 A1      Dec. 25, 2008

Related U.S. Application Data

(60) Provisional application No. 60/936,756, filed on Jun. 22, 2007.

(51) Int. Cl.
*A61K 39/02*    (2006.01)
*A61K 39/38*    (2006.01)
*A61K 48/00*    (2006.01)

(52) U.S. Cl. .................. 424/200.1; 424/93.2; 424/93.4; 424/234.1; 424/817; 424/184.1

(58) Field of Classification Search ........................ None
See application file for complete search history.

(56) References Cited

U.S. PATENT DOCUMENTS

| | | | |
|---|---|---|---|
| 6,019,981 A | 2/2000 | Klesius | 424/234 |
| 6,991,793 B2 | 1/2006 | Shoemaker | 424/184.1 |
| 7,067,122 B1 | 6/2006 | Evans | 424/93.4 |
| 2004/0175407 A1 | 9/2004 | McDaniel | |
| 2004/0234535 A1 | 11/2004 | Shoemaker | |
| 2005/0283001 A1 | 12/2005 | Schweizer | |
| 2006/0073167 A1 | 4/2006 | Oshima | |

OTHER PUBLICATIONS

LaFrentz et al. In: Proceedings of the 48th Western Fish Disease Workshop and AFS Fish Health Section Annual Meeting, Jackson Lake Lodge, Grand Tatin National Park, pp. i-vii and p. 23, Jun. 4-6, 2007.*

O'Farrell et al. Diseases of Aquatic Organisms 43: 199-209, Dec. 2001.*

Daly et al. Diseases of Aquatic Organisms 44: 121-126, 2001.*

* cited by examiner

*Primary Examiner*—S. Devi
(74) *Attorney, Agent, or Firm*—Howard Eisenberg, Esq.

(57) ABSTRACT

Fish are immunized by a mass vaccination method, such as by immersion in water containing an attenuated strain of a pathogenic bacterium that does not effectively cause disease in fish when the non-attenuated pathogenic bacterium is exposed to the fish by immersion. An illustrative example of the method is for immunizing against coldwater disease caused by *Flavobacterium psychrophilum*, which may be attenuated by serial passage in media containing increasing amounts of an antibiotic, such as rifampicin.

10 Claims, 1 Drawing Sheet

VACCINES FOR DISEASES OF FISH

This application claims priority from U.S. Provisional Patent Application Ser. No. 60/936,756, filed on Jun. 22, 2007, which is incorporated herein in its entirety by reference.

It is hereby acknowledged that the U.S. Government has certain rights in the invention described herein, which was supported in part by United States Department of Agriculture grants #2003-33610-13945 and #2004-34468-15199.

FIELD OF THE INVENTION

This invention pertains to the field of vaccines to protect fish from disease caused by bacteria. In a particular embodiment, the invention pertains to the field of vaccines to protect fish from disease caused by bacteria that do not cause disease by immersion, such as coldwater disease caused by *Flavobacterium psychrophilum*.

BACKGROUND OF THE INVENTION

*Flavobacterium psychrophilum* is a Gram-negative bacterial fish pathogen that causes bacterial coldwater disease (CWD) and is considered to be one of the most important pathogens affecting salmonid aquaculture due to its wide distribution and economic impact. In the United States, it is estimated that annual losses incurred from CWD in the Pacific Northwest alone are approximately 9.6 and 4 million dollars for commercial aquaculture of rainbow trout (*Oncorhynchus mykiss* Walbaum) and conservation aquaculture of salmonid species, respectively.

Preventative measures include the use of management strategies to reduce risk factors such as stress, poor water quality, and cutaneous lesions. Even with these in place, CWD commonly occurs and generally requires treatment. Treatment options are limited and include reducing pathogen concentrations, eliminating the spread of the pathogen, and the use of antibiotics. However, the effectiveness of treatment is usually inconsistent, and there are potential risks of developing antibiotic resistant strains. Therefore, a vaccine to prevent CWD is desired. However, even though the need is great and has long been sought, no vaccines for CWD are currently available.

In order to be commercially useful, a vaccine for fish must be capable of conferring protective immunity against a pathogen when the vaccine is administered by practical methods, such as immersing the fish in water containing the vaccine. Vaccination protocols that require individual handling of fish, such as by injection are not practical for most commercial aquaculture operations.

Immunization with killed bacteria has been attempted with *F. psychrophilum*, and protection obtained by immersion or by injection with the killed bacteria has been minimal.

Better protection has been obtained by administering the killed bacteria by injection in combination with an emulsified adjuvant. However, because such vaccination protocols require individual handling of fish, they are less suitable for most aquaculture applications.

Recently, live attenuated bacterial vaccines have been developed to immunize animals against particular diseases. Direct and random approaches can be used to induce mutations into bacterial pathogens to achieve attenuation. Direct approaches include mutation or deletion of genes involved in metabolic pathways and/or pathogenesis, while random approaches include genetic methods such as transposon mutagenesis or the use of chemicals such as antibiotics. In the latter method, bacteria are cultured on or in a medium containing a chemical compound that induces one or more non-lethal mutations in the bacteria, while maintaining the protective immunogenicity of the bacteria.

Antibiotics that promote mutations in bacteria have been found to be useful in the development of attenuated bacteria. The development of resistance to high concentrations of the antibiotic may be correlated with changes in the genotype or phenotype of the bacteria. Such changes are often associated with attenuation of the bacteria while maintaining the immunogenicity of the organism.

One such antibiotic that has been shown to be useful in creating attenuated bacteria is rifampicin. Rifampicin is a broad spectrum antibiotic that inhibits bacterial DNA-dependent RNA polymerase.

A rifampicin-resistant attenuated live vaccine was developed to protect cattle against the effects of infection with *Brucella abortus*. The development of this vaccine was reported in Schurig, Veterinary Microbiology, 28:171-181 (1991). As described in Schurig, the *B. abortus* organism was attenuated by passage of virulent strain 2308 numerous times on medium supplemented with increasing concentrations of rifampicin.

Rifampicin resistant bacteria have also been utilized in the development of attenuated bacterial vaccines for diseases affecting fish. Attenuated rifampicin-resistant live bacterial vaccines for diseases affecting fish are disclosed in Klesius, U.S. Pat. No. 6,019,981; Shoemaker, U.S. Pat. Nos. 6,881, 412; and 6,991,793; and Evans, U.S. Pat. No. 7,067,122.

Klesius discloses an attenuated live bacterial vaccine against enteric septicemia of catfish caused by *Edwardsiella ictaluri*. The rifampicin-resistant bacteria were determined by SDS-PAGE not to produce the O-polysaccharide (O—PS) side chain component of lipopolysaccharide, which is accepted as an important virulence factor of this organism. Klesius discloses that the attenuated strains of *E. ictaluri* differentiated from the parent microorganism because they were resistant to rifampicin and that biochemical characteristics of the attenuated organisms were identical to those of the parent microorganism.

Shoemaker discloses an attenuated live bacterial vaccine against *Flavobacterium columnare*, the causative agent of columnaris disease. Shoemaker discloses that the attenuated strains of *F. columnare* differentiated from the parent microorganism because they were resistant to rifampicin and that biochemical characteristics of the attenuated organisms were identical to those of the parent microorganism.

Evans discloses an attenuated live bacterial vaccine against *Edwardsiella tarda*, the causative agent of *Edwardsiella* septicemia disease. Evans discloses that the attenuated strains of *E. tarda* differentiated from the parent microorganism because they were resistant to rifampicin and that biochemical characteristics of the attenuated organisms were identical to those of the parent microorganism.

Each of the attenuated live vaccines of Klesius, Shoemaker, and Evans was effective when administered to fish by immersion. The effectiveness of immersion vaccination with each of these three vaccines is not surprising because fish are readily infected with each of the three diseases for which the vaccines were developed; enteric septicemia, columnaris disease, and *Edwardsiella* septicemia, by immersion in water containing the causative organisms.

Coldwater disease, unlike the diseases disclosed in Klesius, Shoemaker, and Evans, cannot be effectively introduced into fish by immersion in the absence of some portal of entry. The present inventors have immersed salmonids into water containing high levels of the causative organism of CWD, *F.*

*psychrophilum*, and have been unable to induce disease in this manner. However, if fish were exposed to *F. psychrophilum* by subcutaneous injection, infection with development of disease readily occurred. It is also known that, if fish are wounded prior to the immersion exposure, such as by a pinprick or removal of scales, infection with development of disease occurs.

In view of the fact that infection following exposure to *F. psychrophilum* by immersion does not occur in fish, it would not be expected that vaccination by immersion exposure to attenuated live *F. psychrophilum* would provide protective immunity against CWD.

DESCRIPTION OF THE INVENTION

Figure 1:
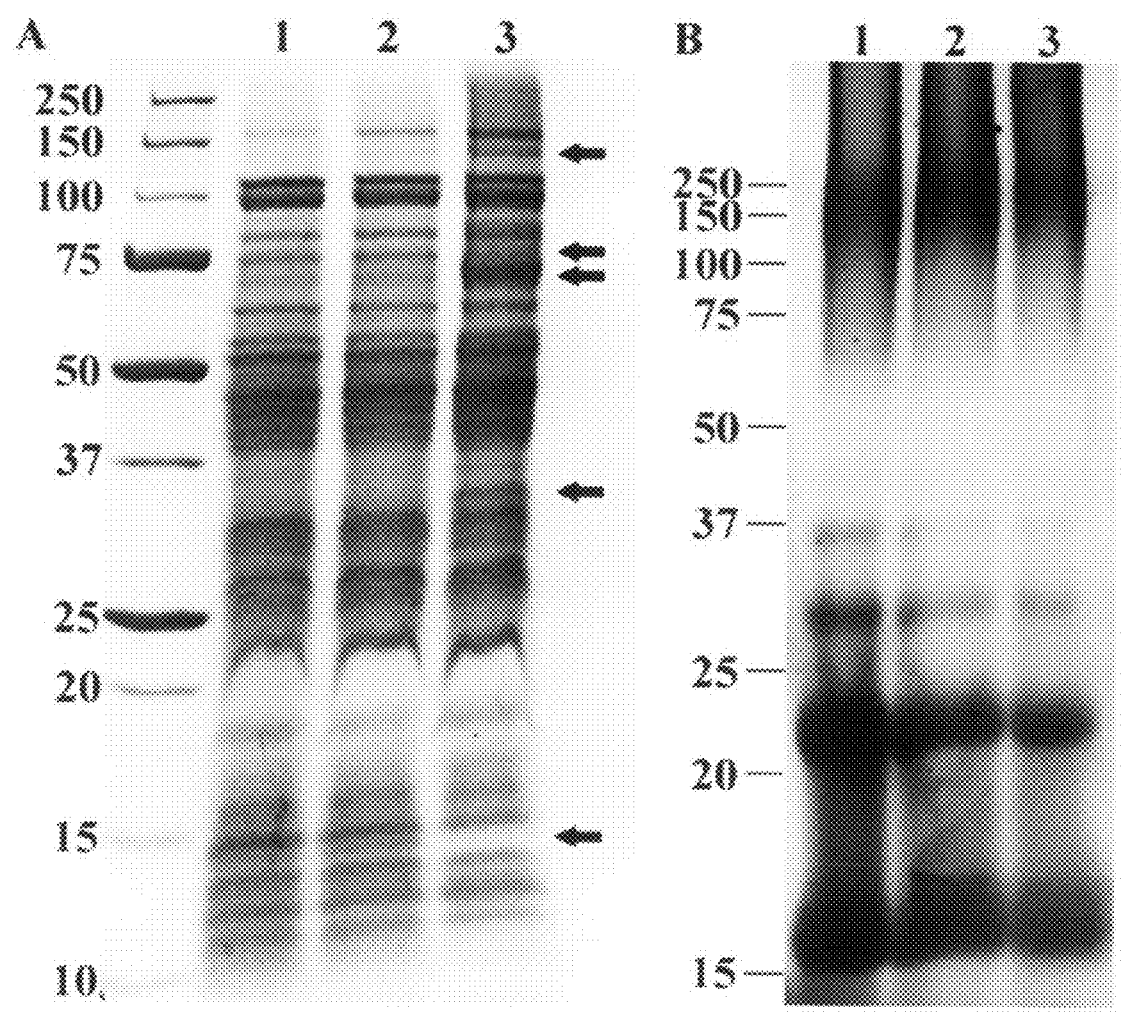
FIG. 1A and 1B shows SDS-PAGE analysis of whole cell lysates (FIG. 1A) and carbohydrate extractions (FIG. 1B) prepared from prepared from the parent *F. psychrophilum* CSF-259-93 strain (Lane 1), 259-93A.16 strain (Lane 2), and 259-93B.17 strain (Lane 3). Whole cell lysate proteins were stained by COOMASSIE and carbohydrate extractions were stained with PRO-Q Emerald 300 LPS Gel Stain. The arrows in (A) indicate protein differences between the strains. Molecular mass markers (kDa) are indicated on the left of each gel.

It has been unexpectedly discovered that protective immunity to CWD can be obtained by mass vaccination, such as by immersing fish in water containing attenuated live *Flavobacterium psychrophilum*. It is conceived, therefore, that fish that are susceptible to CWD and other bacterial diseases of fish, such as bacterial kidney disease (caused by *Renibacterium salmoninarum*), that cannot be induced by immersion techniques can indeed be immunized against such diseases by mass vaccination methods, such as by immersion in water containing the attenuated live members of the causative organism of such diseases.

In one embodiment, the invention is a method for immunizing fish against diseases that are not inducible by immersion techniques. According to this embodiment of the invention, fish are mass vaccinated with an amount of attenuated live bacteria that is effective to provide protection against disease caused by non-attenuated live bacteria of the same species as the attenuated bacteria, wherein immersion without wounding of the fish in water containing the non-attenuated bacteria does not effectively cause disease in the fish. In one embodiment, mass vaccination is by immersion.

The term "mass vaccination" refers to methods of vaccination that do not require handling of individual fish. Methods of mass vaccination include oral, spray, and immersion delivery.

In this specification, immersion is utilized as an illustration of a mass vaccination method. It is postulated that successful vaccination by immersion is indicative of successful vaccination by other mass vaccination methods because spray delivery is similar to immersion delivery and oral delivery provides internalization of vaccine for uptake in the lower gastrointestinal tract. Therefore, although the invention is illustrated with immersion, it is understood that the other mass vaccination methods of fish are included within the scope of the invention.

The term "wounded" as used herein means having a non-physiologic portal of entry to bacteria in water. Examples of wounds include lacerations, punctures, and traumatic removal of one or more fins or scales.

The term "does not effectively cause disease" in reference to the immersion of fish in water containing an infectious bacterium as used herein means that less than 10% of fish immersed for 30 minutes in water at 15° C. containing $1 \times 10^5$ CFU (colony forming units) per ml of the bacterium will become infected with the bacterium and manifest signs of disease due to infection with the bacterium.

The term "attenuated" as used herein in reference to bacteria means that the bacteria has reduced virulence compared to that of wild-type non-attenuated bacteria of the same species. In the case of attenuated bacteria that have no capability to cause disease, such bacteria may be referred to herein as "completely attenuated."

Fish that may be treated by the method of the invention include any fish that is susceptible to infection and disease caused by the particular organism. The fish may be a marine or salt-water fish. Examples of suitable fish for the method of invention include salmonids (*Oncorhynchus* sp. and *Salmo* sp.), American, European, and Japanese eels (*Anguilla* sp.), tilapia (*Oreochromis* sp.), striped bass and hybrid-striped bass (*Morone chrysops*. and *M. saxatilis*), flounders (*Seriola* sp.), seabream (*Sparus* sp.), sea perch (*Lates calcarifer*), the estuarine grouper (*Epinephelus tawine*), walleye (*Stitzostedion vitreum*), channel catfish (*Ictalurus punctutus*), centrachids (such as largemouth bass, *Micropterus salmoides*), brown bullheads (*Nebulosus* sp.), fat head minnows (*Pimephales promelas*), golden shiners (*Netemigonus crysoleucas*), goldfish (*Carassius auratus*), carp (*Cyprinus carpio*), and aquarium fish species such as black mollies (*Poecilia sphenops*) and platies (*Xiphosphorus maculatus*). Species affected specifically by CWD include all salmonids. The pathogen has also been reported in non-salmonid species, such as eel *Anguilla* sp., sea lamprey *Petromyzon marinus*, carp *Cyprinus carpio*, tench *Tinca tinca*, crucian carp *Carassius carassius*, goldfish *C. auratus*, ayu *Plecoglossus altivelis*, pale chub *Zacco platypus*, perch *Perca fluviatilis*, and roach *Rutilus rutilus*.

The water in which the fish are immersed may be fresh water, salt-water, or brackish, depending on the variety of fish to be treated and the natural habitat of the fish.

The amount of bacterial organisms that are delivered to the fish is an amount that is effective to provide protection against disease caused by the bacteria. For example, if delivery is by immersion, the amount of bacteria in the water in which the fish are immersed is effective to provide protection. In a preferred embodiment of immersion delivery, the amount of bacteria in the water is greater than $1 \times 10^4$ cfu/ml. More preferably, the amount of bacteria is greater than $1 \times 10^5$ cfu/ml. Even more preferably, the amount of bacteria is greater than $1 \times 10^6$ cfu/ml. If desired, the amount of bacteria may be $1 \times 10^7$ cfu/ml, or $1 \times 10^8$ cfu/ml, or even higher.

The fish are immersed in the water, or sprayed with a fluid, containing the attenuated live bacteria for a time that is sufficient for the development of protection against disease caused by non-attenuated bacteria of the same species. Generally, immersion times between 15 seconds and several hours are suitable for the method of the invention. Preferably, the immersion time is between 1 minute and two hours. More preferably, immersion time is between 15 minutes and 2 hours. A most preferred immersion time is between 30 minutes and 1 hour.

For purposes of this invention, protection against disease due to the method of the invention is considered to have been elicited when complete or partial immunity against the disease has been obtained. Immunity is considered as having been obtained in a population of treated fish when the level of protection for the population, evidenced by a decrease in the number of infected fish or in severity of disease, is higher in fish that have been treated in accordance with the invention than that of an unvaccinated control group. Preferably, vaccination in accordance with the method of the invention will result in a decrease of 20% in mortality due to the disease or in number of individuals showing clinical signs of the disease compared to unvaccinated controls.

Diseases of fish that may be protected against by the method of the invention include any disease that is caused by a bacterium that does not effectively cause disease in non-wounded fish by immersion. In a preferred embodiment, the disease is coldwater disease, which is caused by *Flavobacterium psychrophilum*. Other diseases that are suitably protected against by the method of the invention include bacterial kidney disease caused by *Renibacterium salmoninarum*. In this specification, *F. psychrophilum* and coldwater disease are utilized as illustrative examples of bacteria and diseases that are suitable for the invention. One of skill in the art will understand that the invention is applicable to organisms and diseases other than *F. psychrophilum* that are not effectively induced by immersion.

The bacteria may be attenuated by any method by which the virulence of the bacteria may be reduced or eliminated. For example, the bacteria may be attenuated by exposing a wild-type strain of the bacteria to radiation or to a chemical compound that promotes mutations. Such methods are known in the art. Antibiotics, such as rifampicin may be used for the development of attenuated strains of infectious bacteria. The use of rifampicin is illustrated as a general method for obtaining an attenuated strain of a bacterium. One of skill in the art will understand that the invention is applicable to methods of attenuation of bacteria other than by the exposure of the organisms to rifampicin.

Rifampicin may be utilized to create attenuated bacteria by serial passaging of wild-type or incompletely attenuated bacteria on or in media containing increasing concentrations of rifampicin. Generally, increasing concentrations of rifampicin are utilized between 5 micrograms/ml to up to about 320 micrograms/ml, although attenuation is generally effective when final concentrations of about 200 micrograms/ml or 250 micrograms/ml.

The attenuated bacteria, such as antibiotic resistant, such as rifampicin resistant, bacteria, may be distinguished from the parent organism because it can survive and reproduce on media containing high concentrations of antibiotic, such as rifampicin, at least up to the final concentration utilized in the attenuation process. Biochemical and physical characteristics of the attenuated bacteria may or may not be identical to those of the parent organism.

Preferably, but not necessarily, there will be at least one difference in protein expression between the parent and attenuated bacteria. Such differences may be determined, for example, by changes in banding patterns such as on SDS-PAGE. The attenuated bacteria may lack expression of proteins that are present in the parent bacteria. Alternatively, or in addition, the attenuated bacteria may express proteins that are not expressed in the parent bacteria. Similarly, banding patterns of lipopolysaccharides and carbohydrates may be identical or different between parent and attenuated strains of bacteria.

Preferably, the attenuated bacteria are completely attenuated and are no longer capable of producing disease in fish. However, there may be circumstances where it is advantageous to vaccinate fish with an incompletely attenuated live bacterial vaccine. Such incompletely attenuated bacteria are within the scope of the present invention.

In another embodiment, the invention is a vaccine for protecting fish against diseases caused by bacteria which, when exposed to non-wounded fish by immersion, does not effectively cause disease in the fish. The vaccine contains an attenuated live bacteria that, when exposed to fish by a mass vaccination method, such as immersion, oral, or spray delivery, in a sufficient amount, provides protection against disease caused by non-attenuated live bacteria of the same species as the attenuated bacteria.

The vaccine may be composed entirely of the attenuated live bacteria with or without culture medium in which the bacteria were grown. If desired, the vaccine may contain constituents in addition to the attenuated bacteria, such as a carrier or vehicle. Suitable carriers include water, physiological saline, mineral oil, vegetable oils, aqueous sodium carboxymethyl cellulose, or aqueous polyvinylpyrrolidone. Vaccine formulations may also contain optional adjuvants, antibacterial agents, or other pharmaceutically active agents as are conventional in the art. Suitable adjuvants include but are not limited to mineral oil, vegetable oils, alum, and Freund's incomplete adjuvant.

A preferred attenuated live bacteria is a member of a strain that has been derived from *F. psychrophilum*. Preferably, the attenuated *F. psychrophilum* is non-virulent, that is completely attenuated. Preferably, the attenuated *F. psychrophilum* has a protein expression profile that differs from that of its parent pathogenic strain. Preferably, but not necessarily, the attenuated live bacteria is resistant to rifampicin.

In a preferred embodiment, the attenuated live bacteria is an isolate designated 259-93.B.17 derived from *F. psychrophilum* that was deposited on May 14, 2008 in the American Type Culture Collection (ATCC) in Manassas, Va. and was assigned ATCC Patent Deposit Designation PTA-9205.

The vaccine may be utilized in accordance with the method of the invention described above to protect fish from diseases of bacteria that, when exposed to non-wounded fish by immersion, do not effectively cause disease in the fish.

In another embodiment, the invention is an attenuated live strain of a bacteria that causes disease in fish but which, when non-wounded fish are exposed to a non-attenuated pathogenic strain of the bacteria, the non-attenuated strain does not effectively cause disease in the fish, wherein exposure of the fish by a mass vaccination method, such as immersion, oral, or spray delivery, to the attenuated live strain of the bacteria protects the fish from disease caused by the non-attenuated strain.

Preferably, the attenuated strain has been derived from *F. psychrophilum*. Preferably, the attenuated strain is non-virulent, that is completely attenuated. Preferably, the attenuated strain has a protein expression profile that differs from that of its parent pathogenic strain. Preferably, but not necessarily, the attenuated strain is resistant to rifampicin.

In a preferred embodiment, the attenuated strain is *Flavobacterium psychrophilum* 259-93.B.17 which was deposited on May 14, 2008 in the American Type Culture Collection (ATCC) in Manassas, Va. and was assigned ATCC Patent Deposit Designation PTA-9205.

The invention is disclosed further in the following non-limiting examples. In the examples that follow, coldwater disease and *Flavobacterium psychrophilum* are utilized as illustrative examples of a disease and a bacterium that are suitable for the invention. One skilled in the art will understand that this is merely an illustration and that the invention is applicable to other diseases of fish and other pathogenic bacteria that cause disease in fish but which do not effectively cause disease when exposed to non-wounded fish by immersion. Similarly, in the following examples, rifampicin is presented as an illustration by which bacteria may be attenuated. One skilled in the art will understand that this is merely an illustration and that other ways of attenuating bacteria are suitable for the invention. Similarly, in the following examples, vaccination according to the invention is illustrated by immersion. One skilled in the art will understand that this is merely an illustration that that other ways of mass vaccination, such as by oral or spray delivery, are suitable for the invention.

EXAMPLE 1

Generation of Attenuated Live Bacterial Strains

A virulent strain of *F. psychrophilum*, CSF-259-93, as described in Sudheesh et al, Diseases of Aquatic Organisms, 74:37-47 (2007), was used as the parent strain to generate rifampicin resistant strains. A previously frozen glycerol stock of CSF-259-93 was plated for isolation on tryptone yeast extract salts (TYES; 0.4% tryptone, 0.04% yeast extract, 0.05% MgSO4-7H2O, 0.05% CaCl2-2H2O, pH 7.2) agar and incubated at 15° C. for 5 d. A single colony was passed to TYES agar containing 5 μg ml−1 rifampicin (Sigma, St. Louis, Mo., USA) and incubated at 15° C. for 6 d. Two of the resulting colonies were randomly selected, designated 259-93A and 259-93B, and independently passed to TYES agar containing increasing concentrations of rifampicin. This process was repeated until the 259-93A and 259-93B strains achieved growth at rifampicin concentrations of 200 and 250 μg ml−1, respectively. This required 16 passages for the 259-93A strain (designated as 259-93A.16) and 17 passages for the 259-93B strain (designated as 259-93B.17). Following each passage, a portion of the growth was harvested, resuspended in sterile 20% glycerol, and frozen at −80° C. The 259-93B.17 strain was deposited on May 14, 2008 in the American Type Culture Collection (ATCC) in Manassas, Virginia and was assigned ATCC Patent Deposit Designation PTA-9205.

EXAMPLE 2

Culture of Bacteria

Growth curves of the CSF-259-93, 259-93A.16 and 259-93B.17 strains were determined. Each strain was pre-cultured in 20 ml TYES broth at 15° C. for 72 h. The optical density of each culture was adjusted to 0.1 at 525 nm using sterile TYES broth. Duplicate culture tubes containing 20 ml TYES broth were inoculated with 50 μl of the adjusted cultures from each strain and incubated at 15° C. for 9 d on an orbital shaker (80 rpm). The growth was monitored daily by measuring the optical densities at 525 nm.

For the challenge and immunization trials, frozen glycerol stocks of each respective strain were plated for isolation on TYES agar and cultured for 96 h at 15° C. Several colonies were passed into 20 ml TYES broth and cultured for 72 h at 15° C. Following 72 h growth, 2 ml of the culture was inoculated into 200 ml TYES broth and cultured for 72 h at 15° C. Bacteria were then harvested by centrifugation at 4300×g for 15 min and the supernatant was removed. Bacterial pellets were resuspended in sterile phosphate buffered saline (PBS; 137 mM NaCl, 2.7 mM KCl, 4.3 mM $Na_2HPO_4.7H_2O$, 1.4 mM $KH_2PO_4$, pH 7.2) at different concentrations depending on the challenge or immunization trial. The number of colony forming units (cfu) $ml^{-1}$ was determined using a 6×6 drop plate method as disclosed in Chen et al, Journal of Microbiological Methods, 55:475-479 (2003), with the exception that TYES agar plates were used and incubated at 15° C. for 96 h.

EXAMPLE 3

Preparation of Whole-Cell Lysates and Carbohydrate Extractions

Whole-cell lysates and carbohydrate extractions of the CSF-259-93, 259-93A.16 and 259-93B.17 strains were prepared and analyzed by sodium dodecyl sulfate-polyacrylamide gel electrophoresis (SDS-PAGE). Each strain was cultured in 200 ml of TYES broth for 72 h at 15° C. Cells were pelleted by centrifugation at 4300×g for 15 min at 4° C. and washed twice with sterile PBS.

Whole-cell lysates were prepared by resuspending approximately 80 mg (wet weight) of cells from each strain into 1 ml sterile PBS and then cell suspensions were sonicated four times for 30 s each at 20% amplitude (Model 500 Sonic Dismembrator, Fisher Scientific, Pittsburgh, Pa., USA). Whole-cell lysates were cooled on ice for 2 min between each 30 s sonication step. Following sonication whole-cell lysates were frozen at −80° C. The protein concentration of each whole-cell lysate was determined using a micro BCA protein assay (Pierce, Rockford, Ill., USA) according to manufacturer's directions.

The carbohydrates from each strain were extracted by resuspending cells into PBS to an optical density of 0.9 at 525 nm. Cells were pelleted from 1.5 ml aliquots and digested with proteinase K (Sigma) according to the method of Hitchcock and Brown, Journal of Bacteriology, 154:269-277 (1983) as modified by LaFrentz et al, Diseases of Aquatic Organisms, 59:17-26 (2004).

EXAMPLE 4

SDS-PAGE

SDS-PAGE was performed according to the method of Laemmli, Nature, 227:680-685 (1970) using a MINI-PROTEAN 3 electrophoresis cell (Bio-Rad, Hercules, Calif., USA). The protein concentrations of the whole-cell lysates from each strain were equalized using sterile deionized water, diluted 1:2 in sample buffer containing 40 mM dithiothreitol (DTT) and then boiled for 5 min. Twenty-five micrograms of protein from each strain were loaded into pre-cast 10-20% gradient polyacrylamide gels (Bio-Rad), electrophoresed at 90 V for 15 min and then at 120 V until the dye front migrated out of the gels. PRECISION PLUS protein standards (Bio-Rad) were used to estimate the molecular mass of proteins. Gels were stained using Bio-Safe COOMASSIE (Bio-Rad) to visualize protein bands according the manufacturer's instructions. Following staining, gels were digitally imaged using a FLUOR-S MultiImager (Bio-Rad).

Undiluted carbohydrate extracts (12 μl) from each strain were loaded into pre-cast 12% polyacrylamide gels (Bio-Rad) and electrophoresed at 100 V until the dye front migrated out of the gels. Gels were stained with PRO-Q Emerald 300 LPS Gel Stain (Molecular Probes, Eugene, Oreg., USA) according to the manufacturer's instructions to visualize the LPS bands. Following staining, gels were digitally imaged using a FLUOR-S MultiImager (Bio-Rad).

EXAMPLE 5

Fish and Rearing Conditions

Two groups of rainbow trout with mean weights of 15 g or 4.6 g were obtained from Clear Springs Foods, Inc. (Buhl, Id., USA) and used in two experimental CWD challenge trials to assess the virulence of the parent and rifampicin resistant strains. Prior to challenge, fish were acclimated for at least one week in 378 liter tanks supplied with specific-pathogen-free 15° C. spring water treated with ultraviolet light. Fish were maintained in 19 liter tanks during bacterial challenges and fed ad libitum daily with an expanded trout feed (Clear Springs Foods, Inc.).

Eyed rainbow trout eggs were obtained from Clear Springs Foods, Inc. or Hayspur State Fish Hatchery (near Gannett, Id., USA) for use in injection and immersion immunization trials, respectively. Upon arrival, eggs were disinfected with 100 ppm iodophor and were reared according to standard practices using 15° C. de-chlorinated municipal water at the University of Idaho (Moscow, Id., USA). Immunized fish were maintained in separate 278 liter tanks and fed 2% body weight per day (Rangen Inc., Buhl, Id., USA). Following bacterial challenge, fish were maintained in 19 liter tanks and fed ad libitum daily.

EXAMPLE 6

Assessment of Virulence

Two experimental CWD challenges were performed to assess the virulence of the parent and rifampicin resistant strains. Rainbow trout were anaesthetized by immersion into ~ 90 mg/l tricaine methanesulfonate (MS-222, Argent Chemicals) and then challenged by subcutaneous injection at the dorsal midline just posterior to the adipose fin with a 30-gauge needle. In trial 1, duplicate groups of 25 rainbow trout (mean weight, 15 g) were challenged by injection with 25 µl of the parent CSF-259-93, 259-93A.16 or 259-93B.17 strains resuspended in PBS to optical densities of 0.6 or 0.4 at 525 nm. A group of mock-infected controls (n=25) were injected with 25 µl of PBS. In trial 2, duplicate groups of 25 rainbow trout (mean weight, 4.6 g) were challenged by injection with 25 µl of the parent CSF-259-93, 259-93A.16 or 259-93B.17 strains resuspended in PBS to an optical density of 0.4 at 525 nm or a 1:10 dilution of this suspension. A group of mock-infected controls (n=25) were injected with 25 µl of sterile PBS.

Mortalities were recorded daily for 28 d and re-isolation of *F. psychrophilum* was attempted on a minimum of 20% of the daily mortalities by inoculating spleen tissue onto TYES agar. The plates were incubated at 15° C. for 7 d, examined for yellow-pigmented bacteria phenotypic of *F. psychrophilum* and recorded as positive or negative. The cumulative percent mortality (CPM) was calculated for each strain at the challenge doses tested.

EXAMPLE 7

Immunization Trials

A. Injection Delivery

Two groups of 350 rainbow trout (mean weight 2.4 g) were used in the study. Following anesthetization by immersion into ~90 mg per liter tricaine methanesulfonate (MS-222, Argent Chemicals, Redmond, Wash., USA), fish in the treatment group were injected intraperitoneally (ip) using a 30-gauge needle with 50 µl containing approximately $8.3 \times 10^6$ cfu fish$^{-1}$ of the 259-93B.17 strain and fish in the control group were injected ip with 50 µl of PBS as a mock immunization. At 5 weeks post-immunization, fish in the treatment group were booster immunized by ip injection with 50 µl containing approximately $6.9 \times 10^6$ cfu fish$^{-1}$ of the 259-93B.17 strain and fish in the control group were injected ip with 50 µl of PBS.

At 8 and 15 weeks post-immunization, rainbow trout were challenged by subcutaneous injection (25 µl) with the parent CSF-259-93 *F. psychrophilum* strain. At 8 weeks post-immunization, triplicate groups of 25 fish from the treatment and control groups were challenged at two doses, corresponding to $4.5 \times 10^6$ and $2.1 \times 10^6$ cfu fish$^{-1}$. At 15 weeks post-immunization, triplicate groups of 25 fish from the treatment and control groups were challenged with one dose, corresponding to $1.8 \times 10^6$ cfu fish$^{-1}$. In each trial, mock infected controls (n=25 fish per treatment or control group) were injected with 25 µl of sterile PBS. Mortalities were monitored as described above. The CPM was determined for the treatment and control groups at each challenge dose, and relative percent survival (RPS) of the treatment group was determined.

Serum samples were obtained from rainbow trout in the treatment and control groups prior to immunization, at the booster immunization, and prior to both bacterial challenges as previously described to determine specific antibody titers using an enzyme-linked immunosorbent assay (ELISA). Prior to immunization, serum was collected from 25 randomly selected fish (five pools of 5 fish). At the booster immunization and prior to both bacterial challenges, serum was collected from 30 randomly selected fish (ten pools of 3 fish) from both treatment and control groups.

B. Immersion Delivery

An immersion immunization trial with the 259-93B.17 strain was performed. Three groups of approximately 100 rainbow trout (mean weight, 3.4 g) were used. One group was immunized by immersion into water containing $1.4 \times 10^8$ cfu per ml of the 259-93B.17 strain for 1 h with aeration. The second group was immunized identically with the exception that each fish was wounded by removal of the adipose fin just prior to immunization. The control group was mock immunized by immersion into water diluted with sterile TYES media (1:4 dilution) for 1 h. At 4 weeks post-immunization, both treatment groups were booster immunized by immersion into a solution of water containing $9.7 \times 10^7$ cfu per ml of the 259-93B.17 strain for 1 h. The control group was mock immunized as described above.

At 10 weeks post-immunization, duplicate groups of 20 fish from each group were challenged by subcutaneous injection (25 µl) with the parent CSF-259-93 *F. psychrophilum* strain at two doses, corresponding to $2.0 \times 10^6$ and $3.3 \times 10^5$ cfu per fish. Mock infected controls (n=20 fish per treatment or control groups) were injected with 25 µl of sterile PBS. Mortalities were monitored as described above and the CPM and RPS was determined for each group.

EXAMPLE 8

ELISA

Specific antibody titers against *F. psychrophilum* in serum samples were determined by an ELISA assay. Briefly, pooled serum samples obtained from treatment and control rainbow trout were serially diluted in doubling dilutions from 1:100 to 1:6400 in PBS containing 0.02% sodium azide, applied to 96-well plates coated with *F. psychrophilum* antigen and specific antibodies were detected as described by LaFrentz et al, Journal of Fish Disease 25:703-713 (2002). The titer was defined as the reciprocal of the highest dilution exhibiting an optical density of at least two times greater than the negative control. The negative control consisted of a pool of equal volumes of serum sampled from the five 5-fish pools collected from fish prior to immunization (see Example 7).

EXAMPLE 9

Statistical Analyses

The mean CPM data from all challenges were normalized using the arcsine square root transformation. CPM data from strain virulence and immunization studies were analyzed by one-way analysis of variance (ANOVA) with Tukey's test for pairwise comparisons or Student's t-test, as appropriate. Serum antibody titers from immunized and control groups were $\log_{10}$ transformed and then analyzed by a Student's t-test. Differences were considered significant when $P<0.05$. Data were analyzed and graphically represented using Graph-Pad Prism (version 2.01, GraphPad Software, San Diego, Calif., USA).

EXAMPLE 10

Growth Comparison

Growth curves of the parent *F. psychrophilum* CSF-259-93, 259-93A.16, and 259-93B.17 strains were determined in TYES broth at 15° C. The lag and exponential growth phases were similar for all strains from 0 to 3 d post-inoculation. Following 3 d, the rifampicin resistant strains grew at a slower rate than the parent strain and the final cell densities were lower.

EXAMPLE 11

Characterization of Proteins and Carbohydrates

Whole-cell lysates and carbohydrate extractions were prepared from each strain and analyzed by SDS-PAGE, see FIG. 1. As shown in FIG. 1A, the 259-93B.17 strain exhibited 5 differentially expressed proteins, as indicated by changes in banding patterns, when compared to the parent CSF-259-93 and 259-93A.16 strains. The 259-93B.17 strain exhibited upregulated expression of proteins with approximate molecular masses of 145, 69, and 33 kDa. Additionally, this strain lacked two proteins with approximate molecular masses of 75 and 14 kDa that were present in the other strains. There were no differences in protein banding patterns between the parent CSF-259-93 and 259-93A.16 strains.

As shown in FIG. 1B, the lipopolysaccharide (LPS) banding patterns were identical among the three strains although there were minor variations in band intensities. All strains possessed 5 LPS bands with approximate molecular masses of 16, 23, 29, 36, and 43 kDa and also contained minor quantities of glycocalyx carbohydrates, visualized as a ladder of fine repeating bands with molecular masses greater than 60 kDa.

EXAMPLE 12

Bacterial Challenge

Rainbow trout were experimentally challenged with the parent CSF-259-93, 259-93A.16, and 259-93B.17 *F. psychrophilum* strains to determine if the rifampicin resistant strains were attenuated. Table 1 shows the cumulative percentage mortality (CPM)±standard error of the mean (SEM) among rainbow trout following experimental challenge with the parent CSF-259-93, 259-93A.16, and 259-93B.17 *F. psychrophilum* strains. CPM values with different superscripts indicate a significant difference at $P<0.05$.

TABLE 1

| *F. psychrophilum* Strain | Trial 1 15.0 g Rainbow Trout | | Trial 2 4.6 g Rainbow Trout | |
|---|---|---|---|---|
| | CPM ± SEM OD 0.4 | CPM ± SEM OD 0.6 | CPM ± SEM 1:10 OD 0.4 | CPM ± SEM OD 0.4 |
| CSF-259-93 | $66.0^a \pm 18.0$ | $78.0^a \pm 10.0$ | $18.9^a \pm 2.9$ | $54.0^a \pm 10.0$ |
| 259-93A.16 | $28.4^{a,b} \pm 7.6$ | $61.4^a \pm 9.4$ | $2.0^{a,b} \pm 2.0$ | $31.2^a \pm 0.8$ |
| 259-93B.17 | $2.0^b \pm 2.0$ | $0.0^b \pm 0.0$ | $0.0^b \pm 0.0$ | $0.0^b \pm 0.0$ |

As shown in Table 1, the results demonstrated complete attenuation of the 259-93B.17 strain and reduced virulence of the 259-93A.16 strain at the challenge doses tested. At the high dose in trial 1, the CPM of fish challenged with the 259-93B.17 strain was significantly different than the CPM of fish challenged with the parent CSF-259-93 and 259-93A.16 strains ($P<0.05$), while there were no significant differences between the CPM of fish challenged with the parent CSF-259-93 and 259-93A.16 strains. Similar mortality trends were observed at the lower challenge dose in trial 1 and also in trial 2 which used rainbow trout with a mean weight of 4.6 g.

Challenge mortalities exhibited typical signs of *F. psychrophilum* infections including necrotic lesions at the site of injection and eroded/frayed fins. Yellow-pigmented bacteria phenotypically consistent with *F. psychrophilum* were re-isolated from 93% (50/54) and 86% (24/28) of the mortalities examined in trials 1 and 2, respectively. There were no mortalities in the mock-infected control groups.

EXAMPLE 13

Immunization Trial Results

A. Injection Immunization Trial

Table 2 shows cumulative percent mortality (CPM)±standard error of the mean (SEM) and relative percent survival (RPS) among rainbow trout immunized by ip injection as described in Example 7A following challenge with the parent CSF-259-93 *F. psychrophilum* strain at 8 and 15 weeks post-immunization. Fish given mock immunizations with PBS sustained high CPM (nearly 100%) upon challenge with the parent CSF-259-93 strain, whereas fish immunized with the 259-93B.17 strain exhibited a significantly decreased CPM at both 8 and 15 weeks post-immunization ($P<0.05$). Relative percent survival values of up to 45% were observed. CPM values with different superscripts indicate a significant difference at $P<0.05$.

TABLE 2

| Treatment | Week 8 Mean CPM ± SEM and (RPS) | | Week 15 Mean CPM ± SEM and (RPS) |
|---|---|---|---|
| | $2.1 \times 10^6$ cfu fish$^{-1}$ | $4.5 \times 10^6$ cfu fish$^{-1}$ | $1.8 \times 10^6$ cfu fish$^{-1}$ |
| PBS | $98.7^a \pm 1.3$ | $97.3^a \pm 2.7$ | $96.0^a \pm 2.3$ |
| 259-93B.17 | $54.1^b \pm 2.1$ (45.2) | $67.1^b \pm 2.5$ (31.1) | $68.0^b \pm 2.3$ (29.2) |

Challenge mortalities exhibited typical signs of *F. psychrophilum* infection. Yellow-pigmented bacteria phenotypically characteristic of *F. psychrophilum* were reisolated from 98% (96/98) and 95% (52/55) of the mortalities examined at the 8 and 15 weeks post-immunization challenges, respectively. There were no mortalities in the mock-infected control groups.

Immunization of rainbow trout with the live 259-93B.17 strain elicited specific antibody responses against *F. psychrophilum* as determined by ELISA. There were no significant differences in the serum antibody titers between treatment and control fish (P>0.05) at the time of booster immunization. At 8 and 15 weeks post-immunization, there were significant differences in mean serum antibody titers between fish immunized with the 259-93B.17 strain and those injected with PBS (P<0.05). Fish immunized with the live 259-93B.17 strain exhibited mean antibody titers (±standard error of the mean) of 1400±570 and 285±94 at 8 and 15 weeks post-immunization, respectively. Specific antibodies were not detected in any of the pooled serum samples from fish injected with PBS (titer<100).

B. Immersion Immunization Trial

Table 3 shows cumulative percent mortality (CPM)±standard error of the mean (SEM) and relative percent survival (RPS) among rainbow trout immunized by immersion as described in Example 7B following *F. psychrophilum* (CSF-259-93) challenge at 10 weeks post-immunization. Fish (with or without adipose fin removal) were immunized by immersion with the 259-93B.17 strain or mock immunized by immersion into water containing TYES. CPM values with different superscripts indicate a significant difference at P<0.05.

TABLE 3

| | Adipose Fin | Mean CPM ± SEM and (RPS) | |
|---|---|---|---|
| Treatment | Removal | $3.3 \times 10^5$ cfu fish$^{-1}$ | $2.0 \times 10^6$ cfu fish$^{-1}$ |
| TYES | No | $72.5^a \pm 2.5$ | $80.0^a \pm 0.0$ |
| 259-93B.17 | No | $52.5^{a,b} \pm 2.5$ (28) | $77.5^a \pm 7.5$ (3) |
| 259-93B.17 | Yes | $40.0^b \pm 5.0$ (45) | $85.0^a \pm 10.0$ (0) |

Immunization of rainbow trout by immersion with the 259-93B.17 strain also conferred protective immunity following bacterial challenge with *F. psychrophilum* at 10 weeks post-immunization. At the low challenge dose ($3.3\times10^5$ cfu per ml), the CPM of immunized fish (without adipose fin removal) was lower than the CPM of the mock immunized control group (P=0.054). Removal of the adipose fin prior to primary-immunization enhanced protective immunity, and the CPM of fish in this group was significantly different than that of the mock immunized control group (P<0.05) but not significantly different than the CPM of immunized fish that did not have adipose fins removed (P>0.05). Relative percent survival values of 45 and 28% were observed for fish treated with or without adipose fin removal prior to immunization, respectively. At the high challenge dose ($2.0\times10^6$ cfu per ml) there were no significant differences among treatment and control groups.

The invention disclosed in this specification has been illustrated with specific examples, such as particular organism and disease (*Flavobacterium psychrophilum* and coldwater disease), and method of attenuation (antibiotic resistance, particularly rifampicin). One skilled in the art will understand that these examples are merely illustrative and that the scope of the invention is as disclosed herein. Additionally, further modifications, uses, and applications of the invention described herein will be apparent to those skilled in the art. It is intended that such modifications be encompassed in the above description and in the following claims.

The invention claimed is:

1. A vaccine for protecting non-wounded fish against a disease caused by non-attenuated *Flavobacterium psychrophilum* comprising isolated, live attenuated, rifampicin-resistant *Flavobacterium psychrophilum*, wherein when the non-wounded fish are exposed by immersion to a sufficient amount of the live attenuated, rifampicin-resistant *Flavobacterium psychrophilum* in the vaccine, the vaccine provides protection against the disease in the non-wounded fish.

2. The vaccine of claim 1, wherein the live attenuated *Flavobacterium psychrophilum* is completely attenuated.

3. The vaccine of claim 1, wherein the live attenuated *Flavobacterium psychrophilum* is *Flavobacterium psychrophilum* designated 259-93.B.17 and deposited at the American Type Culture Collection on 14 May 2008 as PTA-9205.

4. The vaccine of claim 1, wherein the live attenuated *Flavobacterium psychrophilum* has a protein or carbohydrate profile differing from non-attenuated *Flavobacterium psychrophilum*.

5. An isolated, live attenuated, rifampicin-resistant *Flavobacterium psychrophilum*, which protects non-wounded fish from disease caused by non-attenuated *Flavobacterium psychrophilum* when the non-wounded fish are exposed by immersion to the live attenuated, rifampicin-resistant *Flavobacterium psychrophilum*.

6. The isolated, live attenuated, rifampicin-resistant *Flavobacterium psychrophilum* of claim 5 which is *Flavobacterium psychrophilum* designated 259-93.B.17 and deposited at the American Type Culture Collection on 14 May 2008 as PTA-9205.

7. A method of protecting non-wounded fish against disease caused by non-attenuated *Flavobacterium psychrophilum* comprising administering to the fish by mass immersion an amount of an isolated, live attenuated, rifampicin-resistant *Flavobacterium psychrophilum* sufficient to provide protection to the non-wounded fish against the disease.

8. The method of claim 7, wherein the live attenuated *Flavobacterium psychrophilum* is completely attenuated.

9. The method of claim 7, wherein the live attenuated, rifampicin-resistant *Flavobacterium psychrophilum* is *Flavobacterium psychrophilum* designated 259-93.B.17 and deposited at the American Type Culture Collection on 14 May 2008 as PTA-9205.

10. The method of claim 7, wherein the live attenuated, rifampicin-resistant *Flavobacterium psychrophilum* has a protein or carbohydrate profile differing from non-attenuated *Flavobacterium psychrophilum*.

* * * * *